(12) United States Patent
Lee et al.

(10) Patent No.: US 9,950,308 B2
(45) Date of Patent: Apr. 24, 2018

(54) SUPERABSORBENT POLYMER

(71) Applicant: LG Chem, Ltd., Seoul (KR)

(72) Inventors: Sang Gi Lee, Daejeon (KR); Mi Young Kim, Daejeon (KR); Jong Min Lee, Daejeon (KR); Min Seok Jang, Daejeon (KR)

(73) Assignee: LG Chem, Ltd. (KR)

( * ) Notice: Subject to any disclaimer, the term of this patent is extended or adjusted under 35 U.S.C. 154(b) by 6 days.

(21) Appl. No.: 14/904,155

(22) PCT Filed: Jul. 31, 2014

(86) PCT No.: PCT/KR2014/007068
§ 371 (c)(1),
(2) Date: Jan. 11, 2016

(87) PCT Pub. No.: WO2015/016643
PCT Pub. Date: Feb. 5, 2015

(65) Prior Publication Data
US 2016/0151531 A1  Jun. 2, 2016

(30) Foreign Application Priority Data

Aug. 1, 2013  (KR) .................. 10-2013-0091627
Jul. 31, 2014  (KR) .................. 10-2014-0098044

(51) Int. Cl.
*A61L 15/60*  (2006.01)
*B01J 20/26*  (2006.01)

(52) U.S. Cl.
CPC ............ *B01J 20/267* (2013.01); *A61L 15/60* (2013.01)

(58) Field of Classification Search
None
See application file for complete search history.

(56) References Cited

U.S. PATENT DOCUMENTS

| | | | |
|---|---|---|---|
| 4,734,478 A | 3/1988 | Tsubakimoto et al. | |
| 5,140,076 A | 8/1992 | Hatsuda et al. | |
| 5,760,080 A | 6/1998 | Wada et al. | |
| 5,837,789 A | 11/1998 | Stockhausen et al. | |
| 6,245,410 B1 * | 6/2001 | Hahnle | A61L 15/425 428/132 |
| 6,277,772 B1 * | 8/2001 | Gancet | A61L 15/18 428/327 |
| 7,169,843 B2 | 1/2007 | Smith et al. | |
| 7,179,851 B2 | 2/2007 | Qin et al. | |
| 8,017,549 B2 | 9/2011 | Herfert et al. | |
| 2004/0214946 A1 | 10/2004 | Smith et al. | |
| 2006/0204755 A1 * | 9/2006 | Torii | A61L 15/60 428/402 |
| 2007/0203304 A1 * | 8/2007 | Mitchell | A61L 15/60 525/330.3 |
| 2008/0234645 A1 * | 9/2008 | Dodge | A61L 15/60 604/368 |
| 2009/0131255 A1 | 5/2009 | Ikeuchi et al. | |
| 2009/0239966 A1 | 9/2009 | Matsumoto et al. | |
| 2010/0261604 A1 | 10/2010 | Herfert et al. | |
| 2011/0275513 A1 | 11/2011 | Tian et al. | |
| 2011/0301303 A1 | 12/2011 | Kim et al. | |
| 2012/0083411 A1 | 4/2012 | Ahmed et al. | |
| 2012/0258851 A1 | 10/2012 | Nakatsuru et al. | |
| 2012/0267570 A1 | 10/2012 | Shi et al. | |
| 2012/0309619 A1 | 12/2012 | Kwon et al. | |

FOREIGN PATENT DOCUMENTS

| | | |
|---|---|---|
| CN | 101903441 A | 12/2010 |
| EP | 0443627 A2 | 8/1991 |
| JP | S56-161408 A | 12/1981 |
| JP | S57-158209 A | 9/1982 |
| JP | S57-198714 A | 12/1982 |
| JP | 2009509723 A | 3/2009 |
| KR | 0183511 B1 | 4/1999 |
| KR | 19990071530 A | 9/1999 |
| KR | 20060023116 A | 3/2006 |
| KR | 20070094741 A | 9/2007 |
| KR | 20090123904 A | 12/2009 |
| KR | 20100040858 A | 4/2010 |
| KR | 20110049072 A | 5/2011 |
| KR | 20110092236 A | 8/2011 |
| KR | 20110134333 A | 12/2011 |
| KR | 20120132475 A | 12/2012 |
| KR | 20130096152 A | 8/2013 |
| WO | 2004096303 A2 | 11/2004 |
| WO | 2012143215 A1 | 10/2012 |

OTHER PUBLICATIONS

International Search Report for Application No. PCT/KR2014/007068 dated Nov. 27, 2014.
Hosseinzadeh, H. et al., Preparation and Properties of Carrageenan-g-Poly (Acrylic Acid)/Bentonite Superabsorbent Composite, Journal of Biomaterials and Nanobiotechnology, 2011.
Third Party Observation for Application No. PCT/KR2014/007068 dated Nov. 30, 2015.
Reinhold Schwalm, UV Coatings Basics, Recent Developments and New Applications, Elsevier Science, ISBN-10:0444529799; ISBN-13: 978-0444529794; Dec. 21, 2006.
Industrial Solvents Handbook, Marcel Dekker, Inc. pp. 35-68, 1996.
Directory of Solvents, Blackie Academic & Professional, pp. 22-29, 1996.
Hansen Solubility Parameters in Practice, HSP Basics, Hansen-Solubility.com, 2015.

* cited by examiner

*Primary Examiner* — Robert C Boyle
(74) *Attorney, Agent, or Firm* — Lerner, David, Littenberg, Krumholz & Mentlik, LLP

(57) ABSTRACT

A superabsorbent polymer which has excellent initial absorbency and keeps water from flowing out under load even after the passage of a long period of time is provided, in which centrifuge retention capacity (CRC), absorbency under load (AUL), gel bed permeability (GBP), and absorption rate under load of the superabsorbent polymer are optimized within a predetermined range at the same time. Therefore, it is possible to improve physical properties of a final diaper product and to produce a diaper to which an ultra-thin technology is applied.

7 Claims, 3 Drawing Sheets

[FIG. 1]
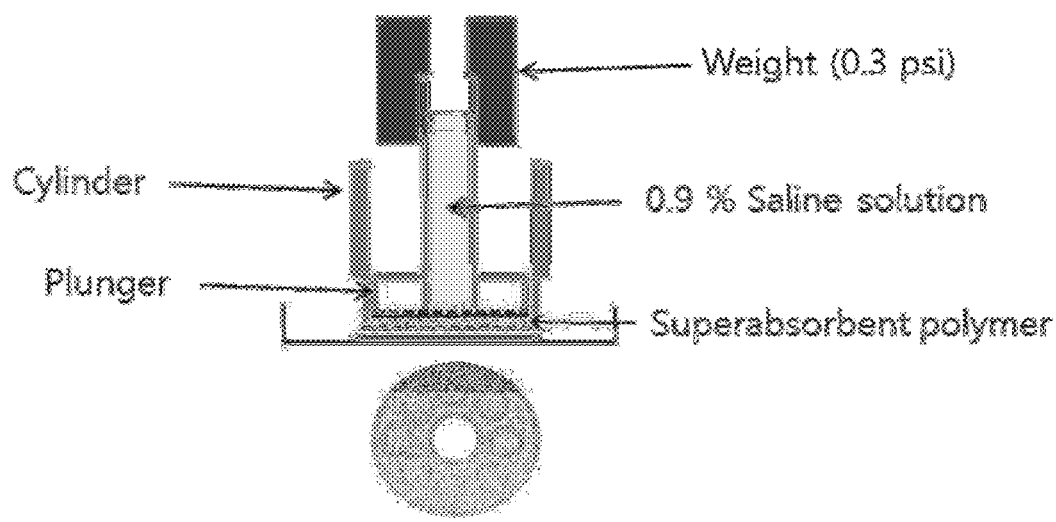

[FIG. 2]
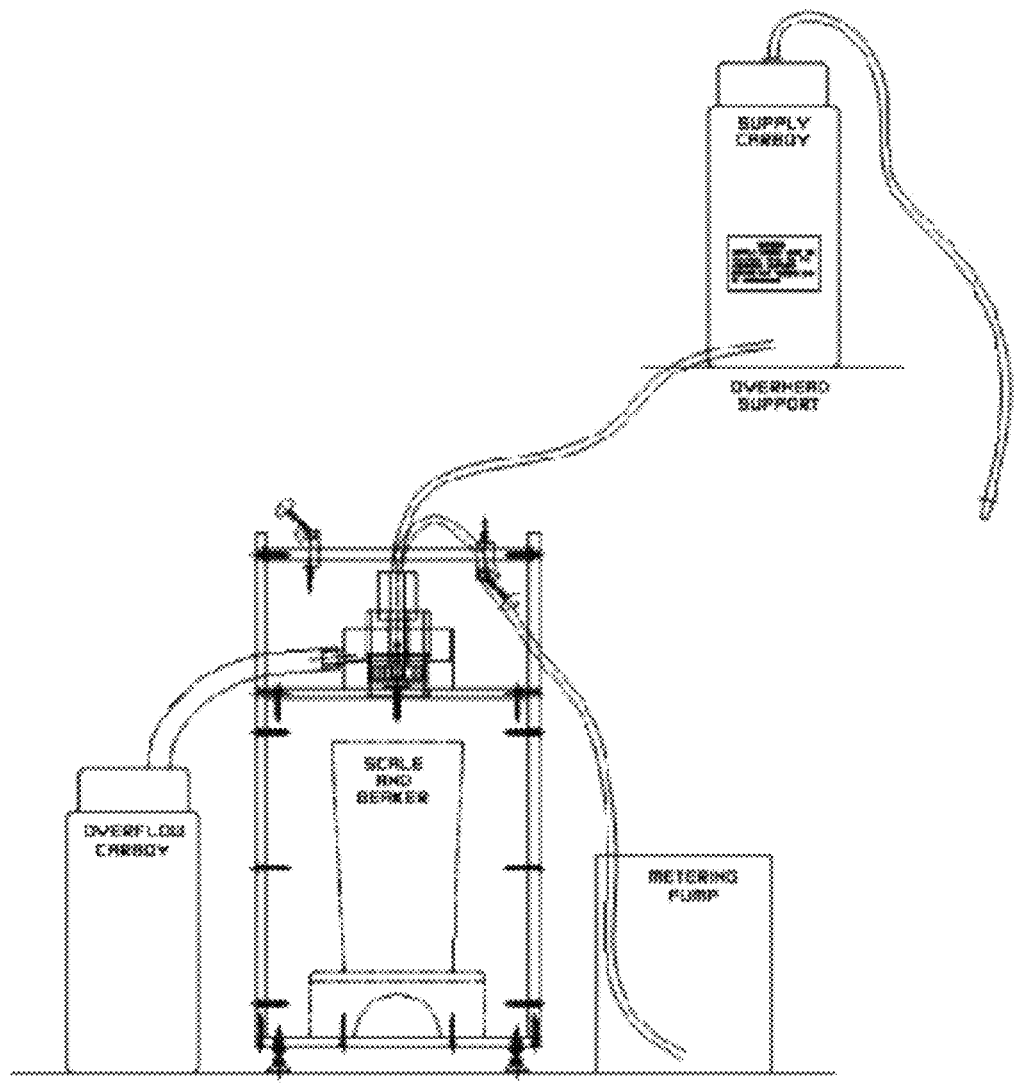

[FIG. 3]
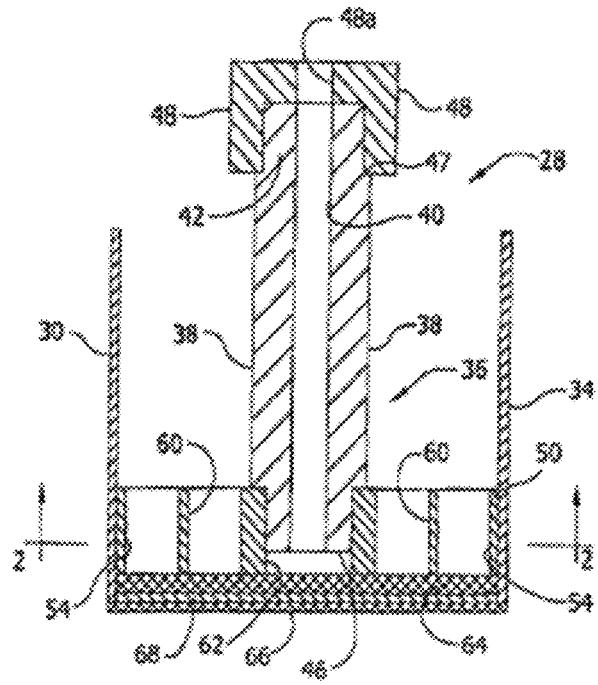
[FIG. 4]
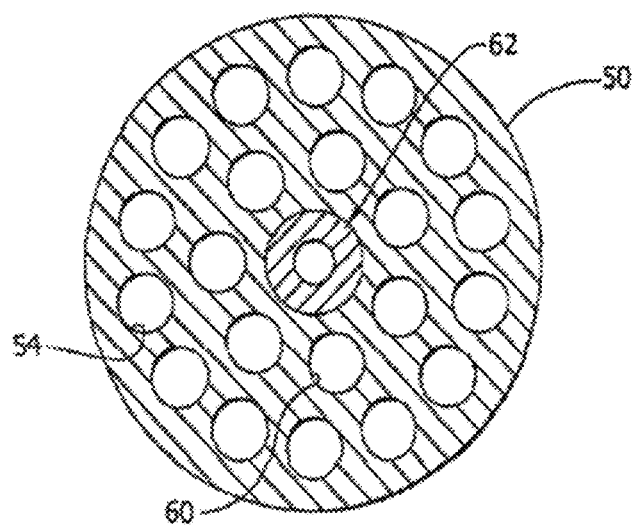

SUPERABSORBENT POLYMER

CROSS-REFERENCE TO RELATED APPLICATION

The application is a national phase entry under 35 U.S.C. § 371 of International Application No. PCT/KR2014/007068, filed Jul. 31, 2014, which claims priority to Korean Application No. 10-2013-0091627, filed Aug. 1, 2013 and Korean Application No. 10-2014-0098044, filed Jul. 31, 2014, the disclosures of which are incorporated herein by reference

TECHNICAL FIELD

The present invention relates to a superabsorbent polymer which is excellent in basic physical properties such as absorbency, etc., and exhibits a high absorption rate under load.

BACKGROUND ART

A superabsorbent polymer (SAP) is a type of synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, etc., but also for water retaining soil products for gardening, water stop materials for civil engineering and construction, sheets for raising seedling, fresh-keeping agents for food distribution fields, materials for poultices, or the like.

As a preparation process for such superabsorbent polymers, a process performed by reverse phase suspension polymerization or a process performed by solution polymerization has been known. For example, Japanese Patent Laid-open Publication Nos. S56-161408, S57-158209, and S57-198714 disclose the reverse phase suspension polymerization.

The process performed by the solution polymerization further includes a thermal polymerization method in which a polymerization gel is polymerized while being broken and cooled in a kneader equipped with a plurality of shafts, and a photo-polymerization method in which an aqueous solution with a high concentration is irradiated with UV rays onto a belt to be polymerized and dried at the same time.

The water-containing gel polymers thus obtained through the polymerization reaction are generally marketed in a powdery form after drying and pulverization processes.

In the products made of superabsorbent polymers, permeability is an index of determining fluidity of a liquid to be absorbed. Permeability may differ depending on the properties such as particle size distribution of crosslinked polymers, particle shape, and the connectedness of open pores between particles, and surface modification of the swollen gel. Fluidity of the liquid passing through swollen particles differs depending on permeability of the superabsorbent polymer composition. A liquid cannot flow readily through a superabsorbent polymer composition with low permeability.

As one of the methods of increasing permeability of the superabsorbent polymer, there is a method of performing a surface crosslinking reaction after polymerization, in which silica or clay is added together with a surface crosslinking agent. For example, U.S. Pat. Nos. 5,140,076 and 4,734,478 disclose the addition of silica during surface crosslinking of dry superabsorbent polymer powders.

However, while permeability is improved by the addition of silica or clay, there are problems that water retention capacity or absorbency under load is reduced in proportion thereto, and separation from the superabsorbent polymer easily occurs by external physical impact during transport. Further, there has been no development of a superabsorbent polymer which shows a high absorption rate under load while maintaining liquid permeability, water retention capacity, and absorbency under load at a predetermined level or higher, thereby exhibiting a high absorption rate in practice when being applied to diapers, etc.

DISCLOSURE

Technical Problem

The present invention is intended to provide a superabsorbent polymer which has excellent physical properties, in particular, excellent initial absorbency by surface treatment thereof, keeps water from flowing out under load even after the passage of a long period of time to show excellent absorbency, and exhibits a high absorption rate under load.

Further, the present invention is intended to provide a method for preparing the superabsorbent polymer.

Technical Solution

The present invention provides a superabsorbent polymer including a crosslinked polymer that is obtained by surface crosslinking of a powdery base polymer using a diol- or glycol-based compound having 2 to 8 carbon atoms, in which the powdery base polymer is obtained by polymerization of water-soluble ethylene-based unsaturated monomers having acidic groups which are at least partially neutralized, using two or more kinds of internal crosslinking agents, and having centrifuge retention capacity (CRC) of 28 g/g or more, absorbency under load (AUL) at 0.9 psi of 18 g/g or more, gel bed permeability (GBP) of 45 Darcy or more, and an absorption rate under a load of 0.3 psi upon third injection of a 0.9 wt % physiological saline solution of 30 to 200 sec.

Further, the present invention provides a method for preparing the superabsorbent polymer, including the steps of: performing thermal polymerization or photo-polymerization of a monomer composition containing the water-soluble ethylene-based unsaturated monomers having acidic groups which are at least partially neutralized, two or more kinds of internal crosslinking agents having a cure dose of 0.16 to 0.35 J/cm$^2$, a photopolymerization initiator, and a thermal polymerization initiator, so as to prepare a water-containing gel polymer; drying the water-containing gel polymer; pulverizing the dried polymer; and performing a surface crosslinking reaction by adding a compound represented by the following Chemical Formula 1 and polyvalent metal cations to the pulverized polymer:

  [Chemical Formula 1]

wherein $R_1$ and $R_2$ are the same as or different from each other, and are each independently a hydroxyl group, an amine group, an epoxide group, or an isocyanate group; and n is an integer of 1 to 3.

Hereinafter, a superabsorbent polymer and a preparation method thereof will be described in more detail according to specific embodiments of the present invention. However, these are for illustrative purposes only, and the scope of the present invention is not intended to be limited thereby. It will be apparent to those skilled in the art that various modifications may be made thereto without departing from the scope of the invention.

Additionally, the term "including" or "containing" means that it includes a particular component (or particular element) without particular limitations unless otherwise mentioned in the present entire disclosure, and it cannot be interpreted as excluding the addition of the other components.

The present inventors studied a superabsorbent polymer which has excellent initial absorbency and keeps water from flowing out under load even after the passage of a long period of time so as to show excellent absorbency, and as a result, they found that when centrifuge retention capacity (CRC), absorbency under load (AUL), gel bed permeability (GBP), and absorption rate under load of the superabsorbent polymer are optimized within a predetermined range at the same time, it is possible to improve physical properties of a final diaper product and to produce a diaper to which an ultra-thin technology is applied, thereby completing the present invention.

According to an embodiment of the present invention, provided is a superabsorbent polymer which has excellent initial absorbency and keeps water from flowing out under load even after the passage of a long period of time so as to show excellent absorbency. In the superabsorbent polymer of the present invention, centrifuge retention capacity (CRC) is 28 g/g or more, absorbency under load (AUL) at 0.9 psi is 18 g/g or more, gel bed permeability (GBP) is 45 Darcy or more, and absorption rate under a load of 0.3 psi upon third injection of a 0.9 wt % physiological saline solution is 30 to 200 sec.

In particular, the superabsorbent polymer of the present invention exhibits superior physical properties, in particular, has superior initial absorbency and keeps water from flowing out under load even after the passage of a long period of time so as to show superior absorbency by performing photo-polymerization and thermal polymerization using two or more kinds of internal crosslinking agents, such as polyethylene glycol diacrylate, as described below. Therefore, the superabsorbent polymer of the present invention which satisfies the specific parameter properties can be widely used not only for various hygiene products, but also for water retaining soil products for gardening, water stop materials for civil engineering and construction, sheets for raising seedling, fresh-keeping agents for food distribution fields, materials for poultices, or the like.

As described above, the present invention provides a synergistic effect by a combination of physical properties of optimizing centrifuge retention capacity (CRC), absorbency under load (AUL), gel bed permeability (GBP), and absorption rate under load of the superabsorbent polymer at the same time. Therefore, the present invention may induce excellent physical properties and comfortable wearing sensation during manufacture of the absorber.

In the superabsorbent polymer of the present invention, the centrifuge retention capacity (CRC) in the physiological saline solution may be represented by the following Equation 1:

$$CRC(g/g) = \{[W_2(g) - W_1(g)]/W_0(g)\} - 1 \quad \text{[Equation 1]}$$

wherein $W_0(g)$ is the weight (g) of the absorbent polymer, $W_1(g)$ is the weight of the apparatus, which is measured after draining water off at 250 G for 3 min using a centrifuge without an absorbent polymer, and $W_2(g)$ is the weight of the apparatus including the absorbent polymer, which is measured after immersing the absorbent polymer in a 0.9 wt % physiological saline solution at room temperature for 30 min and draining water off at 250 G for 3 min using a centrifuge. In particular, $W_0(g)$ as the weight of the absorbent polymer may be the weight of the absorbent polymer which is sieved to 300 to 600 micrometers (μm).

In the superabsorbent polymer, the centrifuge retention capacity (CRC) in the physiological saline solution may be 28 g/g or more, or 28 g/g to 34 g/g, preferably 29 g/g or more, and more preferably 30 g/g or more. If the centrifuge retention capacity (CRC) in the physiological saline solution is less than 28 g/g, there is a problem that water retention capacity of a diaper is reduced to deteriorate physical properties of the diaper.

Further, in the superabsorbent polymer of the present invention, the absorbency under load (AUL) of 0.9 psi in the physiological saline solution may be represented by the following Equation 2:

$$AUL(g/g) = [W_4(g) - W_3(g)]/W_0(g) \quad \text{[Equation 2]}$$

wherein $W_0(g)$ is the weight (g) of the absorbent polymer, $W_3(g)$ is the total weight of the absorbent polymer and the apparatus capable of providing a load for the absorbent polymer, and $W_4(g)$ is the total weight of the water-absorbed absorbent polymer after supplying water for the absorbent polymer under a load (0.9 psi) for 1 hour and the apparatus capable of providing a load for the absorbent polymer.

For example, the absorbency under load (AUL) of 0.9 psi may be measured by placing 0.16 g of the absorbent polymer that is sieved to 300 to 600 μm in a kit for measuring absorbency under load (AUL), and then swelling the polymer under load in a 0.9% saline solution for 1 h while putting a weight of 0.9 psi thereon. At this time, the cell is weighed after 1 h to determine absorbency under load (AUL). In this case, $W_0(g)$ as the weight of the absorbent polymer may be the weight of the absorbent polymer which is sieved to 300 to 600 μm.

In the superabsorbent polymer, its absorbency under load (AUL) of 0.9 psi in the physiological saline solution may be 18 g/g or more, preferably 18.5 g/g or more, and more preferably, 19 g/g or more. It is preferable that the superabsorbent polymer has higher absorbency under load. However, since absorbency under load is a physical property opposite to water retention capacity, the water retention capacity may be reduced by excessively increasing the absorbency under load. It is important to improve absorbency under load and water retention capacity at the same time.

In the present invention, $W_0(g)$ described in Equations 1 to 2 corresponds to the weight (g) of the absorbent polymer, which is applied to each of the physical properties, and they may be the same as or different from each other.

In the superabsorbent polymer of the present invention, its gel bed permeability (GBP) in the physiological saline solution may be 45 Darcy or more, preferably 48 Darcy or more, and more preferably 55 Darcy or more. It is preferable that the superabsorbent polymer has higher gel bed permeability. However, if the gel bed permeability is too high, the water retention capacity or absorbency under load may be reduced. Here, the gel bed permeability (GBP) is expressed as "Darcy" which is a CGS unit of permeability. For example, 1 Darcy is the permeability of a solid through which 1 cm² of fluid having a viscosity of 1 cps will flow in 1 s through a section being 1 cm in thickness and 1 cm² in cross-section, if the pressure difference between the two sides of the solid is 1 atm. Permeability has the same units as area, and is expressed in m², since there is no SI unit for permeability. 1 Darcy corresponds to about $0.98692 \times 10^{-12}$ m² or about $0.98692 \times 10^{-8}$ cm². A method of measuring the gel bed permeability is disclosed in US Patent Publication No. U.S. Pat. No. 7,179,851.

The gel bed permeability (GBP) is the permeability of a swollen bed of gel particles (e.g., the surface treated absorbent material or the superabsorbent material prior to being surface treated), under conditions commonly referred to as "free swell" conditions. However, when the permeability of a swollen bed of gel particles (e.g., the superabsorbent material or the absorbent material as those terms are used herein) is measured "under load" conditions which are generally consistent with normal usage loads (e.g., sitting, walking, twisting, etc.) applied to the particles by the wearer, that is, gel bed permeability under load (0.3 psi GBP or 0.3 GBP) may be 2.5 Darcy or more, preferably 2.8 Darcy or more, and more preferably 3.0 Darcy or more. High gel bed permeability under load means high gel strength, which is an index of mimicking permeability under a baby's weight after urination.

Further, the superabsorbent polymer of the present invention has a high absorption rate under load while maintaining the above-described liquid permeability, water retention capacity, and absorbency under load at a predetermined level or higher. In the superabsorbent polymer, in particular, absorption rate under a load of 0.3 psi upon third injection of a 0.9 wt % physiological saline solution may be 30 to 200 sec, preferably 40 to 190 sec, and more preferably, 50 to 180 sec. It is preferable that the superabsorbent polymer has higher absorption rate under load. However, if the absorption rate under load is as low as 200 s, urine absorption rate of the diaper is slow in practice, leading to urine leakage. Particularly, the absorption rate under load of the superabsorbent polymer is an absorption rate which is measured upon third injection of a physiological saline solution, after injecting 2 g of the absorbent polymer under a load of 0.3 psi and repeatedly injecting 10 mL of 0.9 wt % physiological saline solution three times at 3-min intervals.

In the present invention, the absorption rate under load may be measured using an apparatus as shown in FIG. 1. An apparatus equipped with a cylinder (w/o-ring: Mesh #400), a plunger (Mesh #100), and a weight is used to measure the absorption rate under load in a 0.9 wt % physiological saline solution. In the present invention, the apparatus of measuring the absorption rate under load is characterized in that the saline solution is injected into the top of the superabsorbent polymer (layer) in a more similar way to a practical application, unlike the existing method in which the superabsorbent polymer sucks up the saline solution. Further, the absorption rate under load may be measured by repeating the experiment three or more times. In a more specific embodiment, Whatman paper 4 is first spread on the bottom of the cylinder of FIGS. 1, and 2 g of the superabsorbent polymer of the present invention is uniformly spread thereon. Then, a plunger is placed thereon, and a weight (load) of 0.3 psi is applied thereto. Then, 10 mL of 0.9% saline solution is injected into the pore of the plunger, and a time taken for the saline solution to disappear in the hole of the plunger is measured. In the present invention, this procedure is repeated three or more times, and the time (sec) measured upon the third trial is defined as the absorption rate under load. In particular, the existing method of measuring the absorption of the saline solution under load is to measure the absorption by diffusion from the bottom to the top. In contrast, in the method of measuring the absorption rate under load according to the present invention, the saline solution is injected into the top. Injection of the saline solution in this way is very important in that it mimics the diaper practically used, for example, absorption of a baby's urine in the diaper, and performances of diaper products having different properties can be predicted in advance.

In this regard, when the absorption rate under load of the superabsorbent polymer is measured in the above-described method, the superabsorbent polymer absorbs the physiological saline solution at a very high rate in first and second tests. Once the water swelling of the polymer is increased due to sufficient water absorption in the first and second tests, the absorption rate under load may differ depending on the performances of the respective superabsorbent polymers in a third test. As in the superabsorbent polymer of the present invention, when the absorption rate under a load of 0.3 psi upon third injection of 0.9 wt % physiological saline solution is maintained within the optimized range from 30 to 200 sec, the superabsorbent polymer maintains liquid permeability, water retention capacity, and absorbency under load at a predetermined level or higher, and exhibits a high absorption rate under load, and therefore, it exhibits a high absorption property in practice when being applied to diapers, etc.

Meanwhile, the superabsorbent polymer of the present invention may include a crosslinked polymer which is obtained by surface crosslinking of a powdery base polymer using a diol or glycol-based compound having 2 to 8 carbon atoms, in which the powdery base polymer is prepared by polymerizing water-soluble ethylene-based unsaturated monomers having acidic groups which are at least partially neutralized, using two or more kinds of complex internal crosslinking agents.

In addition, since the crosslinking density of the crosslinked polymer may be a factor that affects the absorbency under load (AUL), the base polymer is preferably surface-crosslinked according to the method of the present invention.

The water-soluble ethylene-based unsaturated monomer may include one or more selected from the group consisting of an anionic monomer such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl(meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl (meth)acrylate or (N,N)-dimethylaminopropyl(meth)acrylate, and a quaternary compound thereof. Among them, acrylic acid having acidic groups which are at least partially neutralized with a strong base such as sodium hydroxide, and a salt thereof, may be properly used as the monomer. In the monomer, the acrylic acid may be neutralized at about 50 mol % or more, about 60 mol % or more, or about 70 mol % or more, thereby more effectively achieving the physical properties of the present invention. That is, in the water-soluble ethylene-based unsaturated monomer, a neutralization degree of the acidic groups may be about 50 mol % or more.

Meanwhile, according to another embodiment of the present invention, a method for preparing the above described superabsorbent polymer is provided. The method for preparing the superabsorbent polymer may include the steps of performing thermal polymerization or photo-polymerization of a monomer composition containing the water-soluble ethylene-based unsaturated monomers having acidic groups which are at least partially neutralized, two or more kinds of internal crosslinking agents having a cure dose of 0.16 to 0.35 J/cm², a photopolymerization initiator, and a thermal polymerization initiator, so as to prepare a water-containing gel polymer; drying the water-containing gel polymer; pulverizing the dried polymer; and performing a surface crosslinking reaction by adding a compound represented by the following Chemical Formula 1 and polyvalent metal cations to the pulverized polymer:

  [Chemical Formula 1]

wherein $R_1$ and $R_2$ are the same as or different from each other, and are each independently a hydroxyl group, an amine group, an epoxide group, or an isocyanate group, and n is an integer of 1 to 3.

In particular, a superabsorbent polymer that has superior physical properties, in particular, superior initial absorbency and keeps water from flowing out under load even after the passage of a long period of time so as to show superior absorbency, may be prepared by performing polymerization using two or more kinds of internal crosslinking agents, such as polyethylene glycol diacrylate, and optimizing the surface crosslinking temperature within a particular range, as described above. Thus, the present invention provides a synergistic effect by a combination of physical properties of optimizing centrifuge retention capacity (CRC), absorbency under load (AUL), and gel bed permeability (GBP) of the prepared superabsorbent polymer at the same time.

In the process of preparing the superabsorbent polymer of the present invention, surface crosslinking reaction may be performed by adding one or more substances selected from the group consisting of a substance satisfying $\delta_p<11$ (J/cm³)$^{1/2}$ and a substance satisfying $\delta_H<4.5$ (J/cm³)$^{1/2}$, $\delta_P$ and $\delta_H$ being defined as Hansen solubility parameters.

According to the method for preparing the superabsorbent polymer, a superabsorbent polymer having improved liquid permeability and improved physical properties due to no reduction in water retention capacity or absorbency under load may be prepared.

Further, in the method for preparing the superabsorbent polymer of the present invention, the monomer composition as a raw material of the superabsorbent polymer includes water-soluble ethylene-based unsaturated monomers, the photopolymerization initiator, and the thermal polymerization initiator.

The water-soluble ethylene-based unsaturated monomer may be any monomer that is typically used in the preparation of the superabsorbent polymer without limitation. Herein, one or more monomers selected from the group consisting of an anionic monomer and salts thereof, a nonionic hydrophilic monomer, and an amino group-containing unsaturated monomer, and a quaternary compound thereof may be used.

Specifically, one or more selected from the group consisting of an anionic monomer such as (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl (meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof may be used.

More preferably, acrylic acid or salts thereof, for example, acrylic acid or alkali metal salts such as sodium salts thereof may be used, and it is possible to prepare a superabsorbent polymer having superior physical properties by using these monomers. When the alkali metal salt of acrylic acid is used as the monomer, acrylic acid may be used after being neutralized with a basic compound such as caustic soda (NaOH).

The concentration of the water-soluble ethylene-based unsaturated monomer may be about 20 to about 60% by weight, preferably about 40 to about 50% by weight, based on the monomer composition containing the raw materials of the superabsorbent polymer and a solvent. The concentration may be properly controlled, considering polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be reduced.

In the preparation method of the superabsorbent polymer of the present invention, the thermal polymerization initiator is included, together with the polymerization initiator, and a certain amount of heat is generated by UV irradiation or the like and is also generated with an exothermic polymerization reaction. Therefore, photo-polymerization and thermal polymerization may be performed at the same time.

As the photo-polymerization initiator, a compound capable of forming radicals by light such as UV may be used without limitations in the constitution. For example, one or more selected from the group consisting of benzoin ether, dialkyl acetophenone, hydroxyl alkylketone, phenyl glyoxylate, benzyl dimethyl ketal, acyl phosphine, and a-aminoketone may be used as the photo-polymerization initiator. Meanwhile, as the specific example of acyl phosphine, commercialized Lucirin TPO, namely, 2,4,6-trimethyl-benzoyl-trimethyl phosphine oxide, may be used. More various photo-polymerization initiators are well disclosed in "UV Coatings: Basics, Recent Developments and New Application (Elsevier, 2007)" written by Reinhold Schwalm, p115, however, they are not limited to the above described examples.

The photo-polymerization initiator may be included at a concentration of 40 to 200 ppm, preferably 45 to 180 ppm, and more preferably 50 to 170 ppm in the monomer composition. If the concentration of the photo-polymerization initiator is too low, the polymerization rate may become low. If the concentration of the photo-polymerization initiator is too high, the molecular weight of the superabsorbent polymer may be decreased and its physical properties may not be uniform.

Further, sulfur-containing persulfate-based initiators may be used as the thermal polymerization initiator. Specifically, examples of the persulfate-based initiators may be one or more selected from the group consisting of sodium persulfate ($Na_2S_2O_8$), potassium persulfate ($K_2S_2O_8$), and ammonium persulfate (($NH_4$)$_2S_2O_8$).

The thermal polymerization initiator may be included at a concentration of about 0.05 to about 0.3% by weight, preferably 0.08 to 0.25% by weight (wt %), and more preferably 0.1 to 0.2% by weight in the monomer composition. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may be decreased and its physical properties may not be uniform.

According to an embodiment of the present invention, the monomer composition may include a complex internal crosslinking agent of two or more kinds of internal crosslinking agents as the raw material of the superabsorbent polymer. Such internal crosslinking agent may be a combination of two or more kinds of a crosslinking agent which has one or more of a functional group capable of reacting with a water-soluble substituent of the water-soluble ethylene-based unsaturated monomer and has one or more of an ethylenic unsaturated group; or a crosslinking agent which has two or more of a functional group capable of reacting with the water-soluble substituent of the monomer and/or a water-soluble substituent formed by hydrolysis of the monomer. In this regard, the internal crosslinking agent may have two to three functional groups as described above.

In particular, each of the two or more kinds of the internal crosslinking agents may be selected from the group consisting of multifunctional acrylate-based compounds having a plurality of ethylene oxide groups. The multifunctional acrylate-based compounds having a plurality of ethylene oxide groups may be selected from the group consisting of polyethylene glycol diacrylate (PEGDA), ethoxylated tri methylolpropane triacrylate (ethoxylated-TMPTA), hexanediol diacrylate, triethylene glycol diacrylate.

In terms of internal crosslinking uniformity, the internal crosslinking agent may have a cure dose of 80% or more to 180% or less, based on the cure dose of acrylic acid. Moreover, the internal crosslinking agent may preferably have a cure dose of 90% or more to 160% or less, and more preferably a cure dose of 95% or more to 155% or less, based on the cure dose of acrylic acid. For example, the internal crosslinking agent may have a cure dose of 0.16 to 0.35 J/cm$^2$, preferably 0.18 to 0.32 J/cm$^2$, and more preferably 0.2 to 0.3 J/cm$^2$.

Here, the cure dose of the internal crosslinking agent is the amount of energy required to cure. That is, as the number of the cure dose increases, the amount of energy required to cure is increased. Further, the values representing the cure dose may be measured using a light meter. For example, a lamp of a curing machine with accessories is set at a predetermined luminance, and a sample is loaded on the belt of the curing machine and passed through the UV curing machine. In this regard, the number of passages through the curing machine is evaluated, based on the conveyor speed of the curing machine and light intensity, and total energy after curing of the surface is calculated. Therefore, there is no limitation in the amount of the sample when the cure dose is measured. In a more specific embodiment, upon the measurement, the solution is poured into a 100 mm Petri dish at a thickness of 0.5 cm, which is loaded on the conveyor belt, followed by operation of the belt.

The cure dose values of the several materials which can be used as the internal crosslinking agent are as shown in Table 1 below.

TABLE 1

| Acrylate-based hydrocarbon | Number of acrylic functional groups | Cure dose (mJ/cm$^2$) | Percentage of cure dose to AA (%) |
|---|---|---|---|
| PEGDA | 2 | 200 | 0 |
| HDDA | 2 | 320 | 60 |
| TMP(PO)3TA | 3 | 490 | 145 |

TABLE 1-continued

| Acrylate-based hydrocarbon | Number of acrylic functional groups | Cure dose (mJ/cm$^2$) | Percentage of cure dose to AA (%) |
|---|---|---|---|
| PETTA | 4 | 158 | 21 |
| NPG(PO)2DA | 2 | 153 | 24 |
| TMP(EO)9TA | 3 | 200 | 0 |

PEGDA: Polyethylene glycol diacrylate
HDDA: Hexanediol diacrylate
TMP(PO)3TA: 3 mol % propoxylated TMPTA (Trimethylolpropane triacrylate)
PETTA: Pentaerythritol Triacrylate
NPG(PO)2DA: 2 mol % propoxylated Neopentyl glycol Diacrylate
TMP(EO)9TA: 9 mol % ethoxylated TMPTA (Trimethylolpropane triacrylate)
* Cure dose of AA: 200 mJ/cm$^2$
* Cure dose information provider: Miwon Specialty Chemical Co., Ltd.

In the present invention, since two or more of the compounds having 60% or less of the cure dose of acrylic acid (AA) are selected from the various acrylic hydrocarbon compounds in Table 1, and they are used in combination, it is possible to prepare a superabsorbent polymer which has excellent physical properties, in particular, excellent initial absorbency, and keeps water from flowing out under load even after the passage of a long period of time to show excellent absorbency.

Such complex internal crosslinking agent is included at a concentration of about 0.05 to about 3% by weight based on the monomer composition so as to crosslink the polymerized polymer. The complex internal crosslinking agent may be included at a concentration of preferably about 0.1 to about 2.5% by weight, and more preferably, about 0.15 to about 2% by weight.

In the preparation method of the present invention, the monomer composition of the superabsorbent polymer may further include an additive such as a thickener, a plasticizer, a preservation stabilizer, an antioxidant, etc., if necessary.

The raw materials such as the above-described water-soluble ethylene-based unsaturated monomer, photopolymerization initiator, thermal polymerization initiator, internal crosslinking agent, and additive may be prepared in the form of a solution of the monomer composition which is dissolved in a solvent.

In this regard, a solvent capable of dissolving the above ingredients may be used as the solvent without limitations in the constitution, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

The solvent may be included in a residual amount excluding the above-described components from the total weight of the monomer composition.

Meanwhile, the method for forming a water-containing gel polymer by thermal polymerization or photo-polymerization of the monomer composition is not particularly limited in the constitution, as long as it is a method typically used.

Specifically, the polymerization method is largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt. The above-described polymerization method is an example only, and the present invention is not limited thereto.

In the polymerization process, for example, the thermal polymerization process may be carried out at a polymerization temperature of 35° C. or higher, or at 35 to 90° C., and the photo-polymerization may be carried out at the same time by irradiation of UV light ranging from 100 to 400 nm.

Further, as described above, thermal polymerization is performed by providing hot air to a reactor like a kneader equipped with the agitating spindles or by heating the reactor so as to obtain the water-containing gel polymer. At this time, the water-containing gel polymer may have the size of centimeters or millimeters when it is discharged from the outlet of the reactor, according to the type of agitating spindles equipped in the reactor. Specifically, the water-containing gel polymer may be obtained in various forms according to the concentration of the monomer composition fed thereto, the feeding speed, or the like, and the water-containing gel polymer having a weight average particle size of 2 to 50 mm may be generally obtained.

Meanwhile, as described above, when the photo-polymerization is carried out in a reactor equipped with a movable conveyor belt, the water-containing gel polymer typically obtained may be a water-containing gel polymer in a sheet-type having a width of the belt. In this regard, the thickness of the polymer sheet may vary according to the concentration of the monomer composition fed thereto and the feeding speed. Preferably, the monomer composition is fed so that the polymer sheet has a thickness of about 0.5 to about 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively high thickness.

In this regard, the water-containing gel polymer thus obtained by the method may have typically a water content of about 40 to about 80% by weight. Meanwhile, the term "water content", as used herein, means a water content in the total weight of the water-containing gel polymer, which is obtained by subtracting the weight of the dry polymer from the weight of the water-containing gel polymer. Specifically, it is defined as a value calculated by measuring the weight loss according to evaporation of water in the polymer during the drying process of increasing the temperature of the polymer with infrared heating. In this regard, the water content is measured under the drying conditions which are determined as follows: the temperature is increased from room temperature to about 180° C. and then the temperature is maintained at 180° C., and the total drying time is determined as 20 min, including 5 min for the temperature rising step.

Next, the step of drying the water-containing gel polymer thus obtained is performed.

If necessary, a coarsely pulverizing step may be performed before the drying step, in order to increase the efficiency of the drying step.

In this regard, a pulverizing device applicable may include, but the constitution is not limited to, any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited thereto.

In this regard, the coarsely pulverizing step may be performed so that the water-containing gel polymer has a particle size of about 2 to about 10 mm.

To pulverize the water-containing gel polymer to have a particle size of less than 2 mm is technically not easy due to its high water content, and agglomeration may occur between the pulverized particles. On the other hand, if the polymer is pulverized to have a particle size of more than 10 mm, the effect of increasing the efficiency in the succeeding drying step may be insignificant.

The water-containing gel polymer coarsely pulverized as above or immediately after polymerization without the coarsely pulverizing step is subjected to a drying process. In this regard, the drying temperature of the drying step may be about 150 to about 250° C. When the drying temperature is lower than 150° C., there is a concern that the drying time becomes excessively long or the physical properties of the superabsorbent polymer finally formed may be deteriorated, and when the drying temperature is higher than 250° C., only the surface of the polymer is dried, and thus there is a concern that fine powder may be generated during the subsequent pulverization process and the physical properties of the superabsorbent polymer finally formed may be deteriorated. Therefore, the drying process may be preferably performed at a temperature of about 150 to about 200° C., and more preferably about 160 to about 180° C.

Meanwhile, the drying process may be carried out for about 20 to about 90 min, considering the process efficiency, but is not limited thereto.

Furthermore, any known drying method may be selected and used in the drying step without limitation in the constitution if it can be generally used for drying the water-containing gel polymer. Specifically, the drying step may be carried out by a method of supplying hot air, irradiating infrared rays, irradiating microwaves, irradiating ultraviolet rays, or the like. When the drying step as above is finished, the water content of the polymer may be about 0.1 to about 10% by weight.

Next, the dried polymer obtained from the drying step is subjected to a pulverization step.

The polymer powder obtained from the pulverization step may have a particle size of about 150 to about 850 μm. Specific example of a milling device that may be used to achieve the above particle size may include a pin mill, a hammer mill, a screw mill, a roll mill, a disc mill, a jog mill, or the like, but the present invention is not limited thereto.

The physical properties of the superabsorbent polymer powder finally manufactured after the pulverization step may be properly controlled through a sorting step according to the particle size of the polymer powder obtained from the pulverization. Only a polymer having a particle size of about 150 to about 850 μm is preferably sorted and then selectively applied to the surface crosslinking reaction, and finally, it is commercialized.

Next, surface crosslinking reaction is performed by adding a compound represented by the following Chemical Formula 1 and polyvalent metal cations to the pulverized polymer:

$R_1\text{—}(CH_2)_n\text{—}R_2$  [Chemical Formula 1]

wherein $R_1$ and $R_2$ are the same as or different from each other, and are each independently a hydroxyl group, an amine group, an epoxide group, or an isocyanate group; and n is an integer of 1 to 3.

The surface crosslinking is a step of increasing the crosslinking density in the vicinity of the surface of the superabsorbent polymer particle with regard to the internal crosslinking density of particles. In general, the surface crosslinking agent is applied to the surface of the superabsorbent polymer particle. Therefore, this reaction occurs on the surface of the superabsorbent polymer particle, which improves crosslinking on the surface of the particle without substantially affecting the interior of the particle. Thus, the surface-crosslinked superabsorbent polymer particles have a higher level of crosslinking in the vicinity of the surface than in the interior.

According to the present invention, the compound represented by the following Chemical Formula 1 and polyvalent metal cations are included as the surface crosslinking agent. The compound represented by the following Chemical Formula 1 and polyvalent metal cations may be used singly or in combination of two or more thereof:

$$R_1\text{—}(CH_2)_n\text{—}R_2 \quad \text{[Chemical Formula 1]}$$

wherein $R_1$ and $R_2$ are the same as or different from each other, and are each independently a hydroxyl group, an amine group, an epoxide group, or an isocyanate group; and n is an integer of 1 to 3.

According to the present invention, polyvalent metal cations are added as the surface crosslinking agent, and they are chelated by the carboxylic groups (COOH) of the superabsorbent polymer, thereby further reducing the crosslinking distance.

According to an embodiment of the present invention, surface crosslinking reaction may be performed by further adding one or more selected from the group consisting of a substance satisfying $\delta_P < 11$ $(J/cm^3)^{1/2}$ and a substance satisfying $\delta_H < 4.5$ $(J/cm^3)^{1/2}$, $\delta_P$ and $\delta_H$ being defined as Hansen solubility parameters.

The substance satisfying $\delta_P < 11$ $(J/cm^3)^{1/2}$ may be exemplified by 1,6-hexanediol, propylene glycol, 1,2-hexanediol, 1,3-butanediol, 2-methyl-1,3-propanediol, 2,5-hexanediol, 2-methyl-1,3-pentanediol, and 2-methyl-2,4-pentanediol, and the substance satisfying $\delta_H < 4.5$ $(J/cm^3)^{1/2}$ may be exemplified by 1,2-propylene carbonate. However, the present invention is not limited thereto, and any substance satisfying the range of the parameter is possible, even though it is not described in the following Table 2.

Hansen solubility parameters were developed by Charles Hansen as a way of predicting if one material will dissolve in another to form a solution. They are parameters described in, for example, ⌈INDUSTRIAL SOLVENTS HANDBOOK⌋ (pp.35-68, Marcel Dekker, Inc., published in 1996), ⌈DIRECTORY OF SOLVENTS⌋ (pp. 22-29, Blackie Academic & Professional, published in 1996), or the like.

Typically, cohesive energy should be obtained in order to calculate solubility parameters. In Hansen solubility parameters, cohesive energy affecting the solubility parameters is divided into the following three parameters.

$\delta_D$: solubility parameter due to non-polar dispersion energy (unit: $(J/cm^3)^{1/2}$)

$\delta_P$: solubility parameter due to dipolar energy (unit: $(J/cm^3)^{1/2}$)

$\delta_H$: solubility parameter due to hydrogen bonding energy (unit: $(J/cm^3)^{1/2}$)

$\delta_{tot}$: $((\delta_D)^2+(\delta_P)^2+(\delta_H)^2)^{1/2}$

The above parameters are obtained to determine a distance between Hansen solubility parameters of two materials, thereby calculating a similarity in the solubilities of the two materials. For example, if Hansen solubility parameters of A and B are $(\delta_D^A, \delta_P^A, \delta_H^A)$ and $(\delta_D^B, \delta_P^B, \delta_H^B)$, respectively, a distance (Ra) between Hansen solubility parameters of the two materials can be calculated by the following equation.

$$Ra=(4*(\delta_D^A-\delta_D^B)^2+(\delta_P^A-\delta_P^B)^2+(\delta_H^A-\delta_H^B)^2)^{1/2}$$

As the Ra value is larger, it is likely that similarity between two materials is decreased in terms of solubility.

Hansen solubility parameters of several substances applicable as the crosslinking agent were calculated according to HSPiP program (Hansen Solubility Parameters in Practice, 3rd edition version 3.1 published by Hansen-Solubility.com) developed by Dr. Hansen' group, as shown in Table 2 below.

TABLE 2

| Substance | Hansen solubility parameters (unit: $(J/cm^3)^{1/2}$) | | | |
|---|---|---|---|---|
| | δD | δP | δH | δtot |
| Ethylene glycol | 17 | 11 | 26 | 33 |
| 1,3-Propanediol | 16.8 | 13.5 | 23.2 | 31.7 |
| 1,4-Butanediol | 16.6 | 11 | 20.9 | 28.9 |
| 1,6-Hexanediol | 15.7 | 8.4 | 17.8 | 25.2 |
| Propylene glycol | 16.8 | 10.4 | 21.3 | 29.1 |
| 1,2-Hexanediol | 16 | 7.4 | 16.7 | 24.9 |
| 1,3-Hexanediol | 16.5 | 8.1 | 20.9 | 27.8 |
| 2-Methyl-1,3-propanediol | 16.3 | 9.2 | 22.8 | 29.5 |
| 2,5-Hexanediol | 16 | 7.5 | 23.9 | 29.7 |
| 2-Methyl-1,3-pentanediol | 15.9 | 7.1 | 22.4 | 28.4 |
| 2-Methyl-2,4-pentanediol | 16 | 8.3 | 22.1 | 28.5 |
| Ethylene carbonate | 18 | 21.7 | 5.1 | 28.7 |
| 1,2-Propylene carbonate | 20 | 18 | 4.1 | 27.2 |
| Diethylene glycol | 16.6 | 12 | 19 | 27.9 |
| Triethylene glycol | 16 | 12.5 | 18.6 | 27.5 |
| Tripropylene glycol | 16 | 6.8 | 16.3 | 23.8 |
| Glycerol | 17.4 | 11.3 | 27.2 | 34.2 |

According to one embodiment of the present invention, the surface crosslinking reaction may be performed by further adding porous inorganic materials such as porous silica or clay, alumina, a silica-alumina complex, nanosilica, titania, zinc oxide, or aluminum sulfate, together with the surface crosslinking agent. The porous inorganic materials may be used in a powdery or liquid form. In particular, alumina powder, silica-alumina powder, titania powder, or a nanosilica solution may be used. Further, the porous inorganic materials may be included in an amount of about 0.05 to about 2% by weight, preferably 0.08 to 0.18% by weight (wt %), and more preferably, 0.1 to 0.15% by weight, based on the monomer composition.

With regard to the method of adding the surface crosslinking agent to the polymer, there is no limitation in the constitution. A method of adding and mixing the surface crosslinking agent and the polymer powder in a reactor, a method of spraying the surface crosslinking agent onto the polymer powder, or a method of continuously feeding the polymer and the surface crosslinking agent to a mixer which is continuously operated may be used.

When the surface crosslinking agent is added, a mixture of water and methanol may be further added. When water and methanol are added, there is an advantage that the surface crosslinking agent can be uniformly dispersed in the polymer. In this regard, the content of water and methanol added may be properly controlled based on 100 parts by weight of the polymer, in order to induce uniform dispersion of the surface crosslinking agent, to prevent agglomeration of the polymer powder, and to optimize the surface penetration depth of the crosslinking agent.

The surface crosslinking reaction is allowed to occur by heating the surface crosslinking agent-added polymer particles at about 160° C. or higher for 20 min or longer. In particular, the surface crosslinking process of the present invention may be performed under conditions of a maximum reaction temperature of 190 to 200° C. and a total reaction time of 0.5 to 1 h, and of maintaining the reaction temperature at 160° C. or higher for about 25 min or longer.

A means for raising the temperature for surface crosslinking reaction is not particularly limited. Heating may be performed by providing a heating medium or by directly providing a heat source. At this time, the type of the heating medium applicable may be a hot fluid such as steam, hot air, hot oil, or the like. However, the present invention is not limited thereto. The temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

Before or after the surface crosslinking reaction, Al is added to perform the crosslinking process, or before or after the surface crosslinking reaction, an inorganic material is mixed to perform the crosslinking process. In a method of mixing silica by a dry process, determined silica powder is generally injected to a powdery product in a plastic bag, and shaken from side to side, thereby easily obtaining a dry-processed product. During a process of passing the product through the line in a commercial process, a predetermined amount of silica is injected while stirring the agitating spindles equipped with paddles capable of mixing powder at a high speed, thereby obtaining a dry-processed product.

The superabsorbent polymer obtained according to the preparation method of the present invention may have the improved liquid permeability without deterioration in the physical properties such as water retention capacity and absorbency under pressure, and may exhibit a high absorption rate under load.

In the present invention, it is possible to add and subtract something other than the above description, if necessary, and thus the present invention is not particularly limited thereto.

Advantageous Effects

According to the present invention, when centrifuge retention capacity (CRC), absorbency under load (AUL), and gel bed permeability(GBP) of the superabsorbent polymer are optimized within an excellent range at the same time, it is possible to improve physical properties of a final diaper product, thereby producing a diaper to which an ultra-thin technology is applied.

In particular, the superabsorbent polymer of the present invention can be applied to production of excellent hygiene products with easy and comfortable wearing sensation, because it shows a small amount of rewetting even after the passage of a predetermined time.

BRIEF DESCRIPTION OF THE DRAWINGS

FIG. 1 is a schematic illustration showing an apparatus for measuring absorption rate under load of a superabsorbent polymer according to an embodiment of the present invention;

FIG. 2 is a schematic illustration showing an apparatus for measuring gel bed permeability (GBP) according to an embodiment of the present invention; and FIGS. 3 and 4 are schematic illustrations showing a cylinder and a mesh arrangement for measuring gel bed permeability, respectively.

DETAILED DESCRIPTION OF THE EMBODIMENTS

Hereinafter, the preferred examples are provided for better understanding. However, the following examples are for illustrative purposes only, and the present invention is not intended to be limited by these examples.

Example 1

500 g of acrylic acid was mixed with 11 g of 0.5% IRGACURE 819 initiator (110 ppm, based on a monomer composition) diluted in acrylic acid in a 2 L glass reactor surrounded by a jacket through which a heating medium pre-cooled at 25° C. was circulated, and a solution (solution A) of 26 g of 5% polyethylene glycol diacrylate (PEGDA, molecular weight of 400, Cure Dose of 200 mJ/cm$^2$) diluted with acrylic acid was injected, and a solution (solution B) of 14 g of trimethylolpropane triacrylate containing 9 mol % of 5% ethylene oxide (Ethoxylated-TMPTA, TMP(EO)9TA, M-3190 Miwon Specialty Chemical Co., Ltd., Cure Dose of 200 mJ/cm$^2$) diluted with acrylic acid was injected, and then 800 g of 24% caustic soda solution (solution C) was slowly added dropwise. The acrylic acid neutralization degree in sodium acrylate obtained as a water-soluble ethylene-based unsaturated monomer was 70 mol %.

After confirming that the temperature of the mixture increased to 80° C. or higher by neutralization heat upon mixing the two solutions, the mixture was left until the reaction temperature reached 40° C., and then 54 g of 2% sodium persulfate solution diluted with water was injected.

The solution was poured in a Vat-type tray (15 cm in width×15 cm in length) installed in a square polymerizer which had a light irradiation device installed at the top and was preheated to 80° C., and photoinitiation was performed by light irradiation. At about 25 sec after light irradiation, gel was generated from the surface, and at 50 sec, bubble formation and polymerization occurred at the same time. Then, the reaction was allowed for additional 3 min, and the polymerized sheet was taken and cut in a size of 3 cm×3 cm, and then subjected to a chopping process using a meat chopper so as to prepare crumbs.

The crumbs were dried in an oven capable of shifting airflow up and down. The crumbs were uniformly dried by flowing hot air at 180° C. from the bottom to the top for 15 min and from the top to the bottom for 15 min. After drying, the dried product had a water content of 2% or less.

After drying, the product was pulverized using a pulverizer and sorted by size, and a size of about 150 to about 850 μm was selected to prepare a base polymer. The base polymer thus prepared had a water retention capacity of 36.5 g/g and a water-soluble component of 12.5% by weight.

Thereafter, 100 g of the base polymer was mixed with a crosslinking agent solution which was prepared by mixing 3 g of water, 3 g of methanol, 0.3 g of 1,3 propanediol, and 0.1 g of Aerosil 200, and then surface crosslinking reaction was allowed at 190° C. for 30 min. The resultant was pulverized and sieved to obtain a surface-treated superabsorbent polymer having a particle size of 150 to 850 μm.

100 g of the surface-treated superabsorbent polymer thus obtained was mixed with 0.08 g of Aerosil 200 by a dry process to prepare a dry-processed silica sample.

Example 2

A superabsorbent polymer was prepared in the same manner as in Example 1, except that 0.2 g of Celite was used instead of Aerosil 200 treated by a dry process in Example 1.

Example 3

A superabsorbent polymer was prepared in the same manner as in Example 1, except that for surface treatment of the base polymer obtained in Example 1, 100 g of the base polymer was mixed with a crosslinking agent solution which was prepared by mixing 3 g of water, 1.0 g of ethylene carbonate, and 0.1 g of Aerosil 200, surface crosslinking reaction was allowed at 190° C. for 30 min, and then the resultant was pulverized and sieved to obtain a surface-treated superabsorbent polymer having a particle size of 150 to 850 μm.

Example 4

A superabsorbent polymer was prepared in the same manner as in Example 1, except that for surface treatment of the base polymer obtained in Example 1, 3 g of water, 1.0 g of 1,3-propanediol, and 0.5 g of propylene glycol were used, based on 100 g of the base polymer.

Example 5

In polymerization as in Example 1, a solution (solution A) of 33 g of 5% polyethylene glycol diacrylate (PEGDA, molecular weight 400, Cure Dose 200 mJ/cm$^2$) diluted with acrylic acid and a solution (solution B) of 3 g of 5% hexanediol diacrylate (HDDA, Hexanediol diacrylate, Cure Dose 320 mJ/cm$^2$) diluted with acrylic acid were injected as the internal crosslinking agents. The base polymer thus prepared had a water retention capacity of 37.2 g/g. The subsequent surface crosslinking process was performed in the same manner as in Example 3.

Comparative Example 1

As an example of the single internal crosslinking agent, 55 g of 5% polyethylene glycol diacrylate (PEGDA, molecular weight 400, Cure Dose 200 mJ/cm$^2$) was used in the acrylic acid-containing solution (solution A) to prepare a base. The base polymer thus prepared had a water retention capacity of 36.2 g/g. Other surface treatment processes were performed in the same manner as in Example 1 to prepare a superabsorbent polymer.

Comparative Example 2

As an example of the single internal crosslinking agent, 5% polyethylene glycol diacrylate (PEGDA, molecular weight 400, Cure Dose 200 mJ/cm$^2$) was not used in the acrylic acid-containing solution (solution A), and a solution (solution B) of 38 g of trimethylolpropane triacrylate containing 9 mol % of 5% ethylene oxide (Ethoxylated-TMPTA, TMP(EO)9TA, M-3190 Miwon Specialty Chemical Co., Ltd., Cure Dose of 200 mJ/cm$^2$) diluted was mixed. The base polymer thus prepared had a water retention capacity of 33.2 g/g. Other surface treatment processes were performed in the same manner as in Example 1 to prepare a superabsorbent polymer.

Comparative Example 3

A superabsorbent polymer was prepared in the same manner as in Comparative Example 1, except that 55 g of 5% polyethylene glycol diacrylate (PEGDA, molecular weight 400, Cure Dose 200 mJ/cm$^2$) diluted was mixed and 5 g of D-sorbitol was added in the acrylic acid-containing solution (solution A) at the same time. The base polymer thus prepared had a water retention capacity of 35.5 g/g.

Comparative Example 4

In polymerization as in Example 1, a solution (solution A) of 26 g of 5% polyethylene glycol diacrylate diluted (PEGDA, molecular weight 400, Cure Dose 200 mJ/cm$^2$) and a solution (solution B) of 16 g of trimethylolpropane triacrylate containing 5 mol % of 5% propylene oxide (Propoxylated-TMPTA, TMP(PO)5TA, Miwon Specialty Chemical Co., Ltd., Cure Dose of 490 mJ/cm$^2$) were injected as the internal crosslinking agents. The base polymer thus prepared had a water retention capacity of 38.4 g/g. The subsequent surface crosslinking process was performed in the same manner as in Example 1.

Comparative Example 5

In polymerization as in Example 1, a solution (solution A) of 26 g of 5% polyethylene glycol diacrylate diluted (PEGDA, molecular weight 400, Cure Dose 200 mJ/cm$^2$) and a solution (solution B) of 12 g of 5% pentaerythritol tetraacrylate (PETTA, pentaerythritol triacrylate; Miwon Specialty Chemical Co., Ltd., Cure Dose of 158 mJ/cm$^2$) diluted were injected as the internal crosslinking agents. The base polymer thus prepared had a water retention capacity of 34.3 g/g. The subsequent surface crosslinking process was performed in the same manner as in Example 1.

Experimental Example

Physical properties of the superabsorbent polymers prepared in Examples 1 to 5 and Comparative Examples 1 to 5 were evaluated as follows, and then the physical properties thus measured are shown in the following Table 3.

(1) Particle Size

The particle sizes of the base polymers and the superabsorbent polymers used in Examples 1 to 5 and Comparative Examples 1 to 5 were measured according to EDANA WSP 220.2 (European Disposables and Nonwovens Association, EDANA).

(2) Centrifuge Retention Capacity (CRC)

Water retention capacity by absorbency under no load was measured for the absorbent polymers of Examples 1 to 5 and Comparative Examples 1 to 5 according to EDANA WSP 241.2 (European Disposables and Nonwovens Association, EDANA).

That is, the polymer $W_0$ (g, about 0.2 g) obtained in Examples 1 to 5 or Comparative Examples 1 to 5 was uniformly placed into a nonwoven-fabric-made bag, followed by sealing. Then, the bag was immersed into 0.9% by weight of physiological saline solution at room temperature. 30 min later, the bag was drained at 250 G for 3 min with a centrifuge, and the weight $W_2$(g) of the bag was then measured. Further, the same procedure was carried out using no polymer, and the resultant weight $W_1$(g) was measured.

Thus, CRC (g/g) was calculated from these weights thus obtained, according to the following Equation 1, so as to confirm water retention capacity:

$$CRC(g/g) = \{[W_2(g) - W_1(g)]/W_0(g)\} - 1 \quad \text{[Equation 1]}$$

wherein $W_0(g)$ is the weight (g) of the absorbent polymer, $W_1(g)$ is the weight of the apparatus which is measured after draining water off at 250 G for 3 min with a centrifuge using no absorbent polymer, and $W_2(g)$ is the weight of the apparatus including the absorbent polymer, which is measured after immersing the absorbent polymer in 0.9% by weight of the physiological saline solution at room temperature for 30 min and draining water off at 250 G for 3 min with a centrifuge.

(3) Absorbency Under Load (AUL)

Absorbency under load (AUL) of 0.9 psi was measured for the superabsorbent polymers of Examples 1 to 5 and Comparative Examples 1 to 5.

First, a 400 mesh stainless steel net was installed in the bottom of a plastic cylinder having an internal diameter of 25 mm. The polymer $W_0$ (g, 0.16 g) obtained in Examples 1 to 7 or Comparative Examples 1 to 4 was uniformly scattered on the steel net at room temperature and humidity of 50%, and a piston which can provide a load of 5.1 kPa (0.9 psi) uniformly was put thereon, in which the external diameter of the piston was slightly smaller than 25 mm, there was no gap between the internal wall of the cylinder and the piston, and the jig-jog of the cylinder was not interrupted. At this time, the weight $W_3(g)$ of the device was measured.

After putting a glass filter having a diameter of 90 mm and a thickness of 5 mm in a Petri dish having the diameter of 150 mm, a physiological saline solution composed of 0.90% by weight of sodium chloride was poured in the dish until the surface level became equal to the upper surface of the glass filter. A sheet of filter paper having a diameter of 90 mm was put thereon. The measuring device was put on the filter paper and the solution was absorbed for 1 h under the load. After 1 h, the weight $W_4(g)$ was measured after lifting up the measuring device.

The absorbency under load AUL (g/g) was calculated from the weights thus obtained, according to the following Equation 2:

$$AUL(g/g) = [W_4(g) - W_3(g)]/W_0(g) \quad \text{[Equation 2]}$$

wherein $W_0(g)$ is the weight (g) of the absorbent polymer, $W_3(g)$ is the total weight of the absorbent polymer and the apparatus capable of providing a load for the absorbent polymer, and $W_4(g)$ is the total weight of the water-absorbed absorbent polymer after supplying water for the absorbent polymer under a load (0.9 psi) for 1 hour, and the apparatus capable of providing a load for the absorbent polymer.

(4) Gel Bed Permeability (GBP)

Gel bed permeability (GBP) was measured for the superabsorbent polymers of Examples 1 to 5 and Comparative Examples 1 to 5. A GBP measurement method is described in U.S. Pat. No. 7,179,851.

In particular, the superabsorbent polymer according to the present invention shows particular properties or characteristics when free swell gel bed permeability (GBP) and gel bed permeability under load ("0.3 GBP") are measured. The free swell gel bed permeability test determines the permeability of a swollen bed of a superabsorbent material (e.g., such as separation from an absorbent structure) as Darcy under a given load, after what is commonly referred to as "free swell" conditions. The term "free swell" means that the superabsorbent material is allowed to swell without a restraining load upon absorbing a test solution. The gel bed permeability under load ("0.3 GBP") means the permeability of a swollen bed of gel particles (e.g., such as superabsorbent material or absorbent material as used herein) after restraining the superabsorbent polymer composition under "a restraining load of about 0.3 psi".

Free Swell Gel Bed Permeability (GBP) Test

First, a free swell gel bed permeability (GBP) test determines the permeability of a swollen bed of gel particles (e.g., such as the surface-treated absorbent material or the superabsorbent material prior to being surface-treated), under what is commonly referred to as "free swell" conditions. The term "free swell" means that the gel particles are allowed to swell without a restraining load upon absorbing a test solution as will be described. The term "free swell" means that the superabsorbent polymer is allowed to swell without a restraining load upon absorbing a test solution as will be described. A suitable apparatus for conducting the permeability test is shown in FIGS. 3 and 4, and indicated generally by 28 of FIG. 3. The test apparatus 28 includes a sample container (generally indicated by 30), and a piston (generally indicated by 36).

The piston 36 includes a cylindrical LEXAN shaft 38 having a concentric cylindrical hole 40 bored down the longitudinal axis of the shaft. Both ends of the shaft 38 are machined to provide upper and lower ends (designated as 42, 46, respectively). A weight (indicated by 48) rests on one end 42 and has a cylindrical hole 48a that is bored through at least a portion of its center.

A circular piston head 50 is positioned on the other end 46 and is provided with a concentric inner ring of seven holes 60 (each having a diameter of about 0.95 cm), and a concentric outer ring of fourteen holes 54 (each having a diameter of about 0.95 cm). The holes 54 and 60 are bored from the top to the bottom of the piston head 50. The piston head 50 also has a cylindrical hole 62 bored in the center thereof to receive the end 46 of the shaft 38. The bottom of the piston head 50 may also be covered with a biaxially stretched 400 mesh stainless steel screen 64.

The sample container 30 includes a cylinder 34 and a 400 mesh stainless steel cloth screen 66 that is biaxially stretched to tautness and attached to the lower end of the cylinder. A superabsorbent polymer sample (indicated by 68 in FIG. 3) is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm, and a height of about 10 cm. Drainage holes (not shown) are formed in the sidewall of the cylinder 34 at a height of about 7.8 cm above the screen 66 to allow liquid to drain from the cylinder, thereby maintaining a fluid level in the sample container at about 7.8 cm above the screen 66. The piston head 50 is machined from a LEXAN rod or equivalent material and has a height of about 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is about 2.54 cm in length and about 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is a 0.9 weight percent sodium chloride solution in distilled water. The combined weight of the piston 36 and annular weight 48 equals about 596 g, which corresponds to a pressure applied to the absorbent structure sample 68 of about 0.3 psi or about 20.7 g/cm², over a sample area of about 28.27 cm².

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the gel bed permeability test under "free swell" conditions, the piston 36, with the weight 48 seated thereon, is placed in an empty sample container 30, and the height from the bottom of the weight 48 to the top of the cylinder 34 is measured using a caliper with suitable gauge accuracy to 0.01 mm. It is important to measure the height of each sample container 30 empty and to keep track of which piston 36 and weight 48 is used when using a multiple-test apparatus. The same piston 36 and weight 48 should be used for measurement when the superabsorbent polymer sample 68 is later swollen following saturation.

The sample to be tested is prepared from the superabsorbent material particles which are prescreened through a US standard 30 mesh screen and retained on a US standard 50 mesh screen. As a result, the test sample includes particles sized in the range of about 300 to about 600 µm. The particles can be prescreened by hand or automatically. About 2.0 g of the sample is placed in the sample container 30, and then submerged without the piston 36 and the weight 48 in the test solution for a time period of about 60 min to saturate the sample and allow the sample to swell free of any restraining load.

At the end of this period, the piston 36 and weight 48 assembly is placed on the saturated sample 68 in the sample container 30, and then the sample container 30, piston 36, weight 48, and sample 68 are removed from the solution. The thickness of the saturated sample 68 is determined by again measuring the height from the bottom of the weight 48 to the top of the cylinder 34, using the same caliper or gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of the test solution into the container is adjusted to maintain a fluid height of about 7.8 cm above the bottom of the sample container. The quantity of solution passing through the sample 68 versus time is measured gravimetrically. Data points are collected every second for at least 20 seconds once the fluid level has been stabilized to and maintained at about 7.8 cm in height. The flow rate Q through the swollen sample 68 is determined in units of g/sec by a linear least-squares fit of fluid passing through the sample 68 (in grams) versus time (in seconds). Permeability (Darcy) is obtained by the following Equation 3:

$$K=[Q \times H \times Mu]/[A \times Rho \times P]$$ [Equation 3]

where K is permeability (cm²), Q is a flow rate (g/sec), H is a height of sample (cm), Mu is a liquid viscosity (poise) (about 1 cps for the test solution used with this test), A is a cross-sectional area for liquid flow (cm²), Rho is a liquid density (g/cm³) (for the test solution used with this test) and P is a hydrostatic pressure (dyn/cm²) (normally about 3923 dyn/cm²). The hydrostatic pressure is calculated from the following Equation 4:

$$P=Rho \times g \times h$$ [Equation 4]

where Rho is a liquid density (g/cm³), g is a gravitational acceleration, nominally 981 cm/sec², and h is a fluid height (e.g., 7.8 cm for the permeability test described herein).

Gel Bed Permeability Under Load Test

Gel bed permeability (GBP) under load test (otherwise referred to herein as GBP at 0.3 psi) determines the permeability of a swollen bed of gel particles (e.g., the superabsorbent material or the absorbent material as those terms are used herein), under conditions that are commonly referred to as being "under load" conditions. The term "under load" means that swelling of the particles is restrained by a load generally consistent with normal usage loads applied to the particles (e.g., sitting, walking, twisting, etc.) by the wearer.

More particularly, the gel bed permeability under load test is substantially the same as the free swell gel bed permeability test described previously with the following exception. After about 2.0 g of the sample is placed in the sample container 30 and spread out evenly on the bottom of the sample container, the piston 36 and the weight 48 are placed on the sample within the sample container prior to the sample container (with the piston and weight therein) being submerged in the test solution (0.9 wt % NaCl saline) for a time period of about 60 min. As a result, a 0.3 psi restraining load is applied to the sample as the sample becomes saturated and swells.

(5) Absorption Rate Under Load

Absorption rate under load (Strike through time under load, swelling rate of SAP under load) was measured for the superabsorbent polymers of Examples 1 to 5 and Comparative Examples 1 to 5 by the following method.

First, as shown in FIG. 1, an apparatus equipped with a cylinder (w/o-ring: Mesh #400), a plunger (Mesh #100), and a weight (0.3 psi) was used, and the apparatus for measuring free swell gel bed permeability (GBP) shown in FIG. 3 was used in the test. In this regard, the weight provides a load of 2.07 kPa (0.3 psi) uniformly, in which there was no gap between the internal wall of the cylinder and the weight, and the jig-jog was not interrupted. Further, Whatman paper 4 was spread on the bottom of the cylinder of the apparatus, and 2 g of the superabsorbent polymer was uniformly spread thereon. Then, a plunger was placed thereon, and a weight (load) of 0.3 psi was applied thereto. Then, 10 mL of a 0.9% saline solution at 22° C. was injected into the pore of the plunger, and a time taken for the saline solution to disappear in the hole of the plunger was measured. This procedure is repeated three times, and at each trial, 10 mL of the solution was injected at 3 min intervals. The time (sec) taken for the saline solution to disappear was measured as the absorption rate.

TABLE 3

| | Absorption rate under load (sec) | | | CRC | AUL | GBP | 0.3 GBP |
|---|---|---|---|---|---|---|---|
| | First | Second | Third | (g/g) | (g/g) | (Darcy) | (Darcy) |
| Example 1 | 28 | 93 | 95 | 31.5 | 20.3 | 68 | 3.5 |
| Example 2 | 54 | 115 | 125 | 32 | 18 | 52 | 3.3 |
| Example 3 | 60 | 86 | 102 | 30.8 | 19.5 | 73 | 2.9 |

TABLE 3-continued

| | Absorption rate under load (sec) | | | CRC | AUL | GBP | 0.3 GBP |
|---|---|---|---|---|---|---|---|
| | First | Second | Third | (g/g) | (g/g) | (Darcy) | (Darcy) |
| Example 4 | 58 | 98 | 142 | 31.6 | 19.8 | 65 | 3.2 |
| Example 5 | 62 | 125 | 154 | 30.5 | 19.1 | 70 | 3.1 |
| Comparative Example 1 | 72 | 234 | 276 | 31 | 16 | 35 | 2.4 |
| Comparative Example 2 | 59 | 175 | 243 | 32 | 18.5 | 42 | 1.4 |
| Comparative Example 3 | 95 | 211 | 295 | 31.8 | 18.1 | 32 | 0.8 |
| Comparative Example 4 | 66 | 182 | 212 | 31.2 | 17.7 | 42 | 2.6 |
| Comparative Example 5 | 68 | 193 | 236 | 30.2 | 18.3 | 47 | 2.7 |

As shown in Table 3, the superabsorbent polymers of Examples 1 to 5 according to the present invention show high absorption rate under load, liquid permeability, and excellent absorbency, while having improved liquid permeability, water retention capacity, and absorbency under load, compared to those of Comparative Examples 1 to 5, and they can be used to produce diapers to which an ultra-thin technology is applied.

The invention claimed is:

1. A method for preparing a superabsorbent polymer, comprising:
   thermal polymerizing or photo-polymerizing a monomer composition to form a water-containing gel polymer, wherein the monomer composition contains water-soluble ethylene-based unsaturated monomers having acidic groups which are at least partially neutralized, two or more kinds of internal crosslinking agents having a cure dose of 0.16 to 0.35 J/cm², and a polymerization initiator, wherein the polymerization initiator is a photopolymerization initiator, or a thermal polymerization initiator;
   drying the water-containing gel polymer to form a dried polymer;
   pulverizing the dried polymer to form a pulverized polymer; and
   performing a surface crosslinking reaction by adding a compound represented by the following Chemical Formula 1 and polyvalent metal cations to the pulverized polymer to form a superabsorbent polymer:

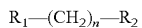    [Chemical Formula 1]

wherein $R_1$ and $R_2$ are each independently a hydroxyl group; and n is an integer of 1 to 3,
   wherein each of the two or more kinds of the internal crosslinking agents is selected from the group consisting of polyethylene glycol diacrylate (PEGDA), ethoxylated trimethylolpropane triacrylate (ethoxylated-TMPTA), hexanediol diacrylate, and triethylene glycol diacrylate,
   wherein the superabsorbent polymer has a centrifuge retention capacity (CRC) of 28 g/g or more, absorbency under load (AUL) of 18 g/g or more at 0.9 psi, gel bed permeability (GBP) of 45 Darcy or more, and an absorption rate under a load of 0.3 psi upon third injection of a 0.9 wt % physiological saline solution of 30 to 200 sec.

2. The method according to claim 1, wherein the internal crosslinking agents are included in an amount of 0.05 to 3% by weight, based on the monomer composition.

3. The method according to claim 1, wherein the photo-polymerization initiator is included in an amount of 40 to 200 ppm, based on the monomer composition.

4. The method according to claim 1, wherein the thermal polymerization initiator is included in an amount of 0.05 to 0.3% by weight, based on the monomer composition.

5. The method according to claim 1, wherein the thermal polymerization initiator is a sulfur-containing persulfate compound.

6. The method according to claim 1, wherein the water-soluble ethylene-based unsaturated monomers having acidic groups which are at least partially neutralized has a neutralization degree of the acidic groups of 50 mol % or more.

7. The method according to claim 1, wherein during the performing of the surface crosslinking reaction, a porous inorganic material is added.

* * * * *